United States Patent
Ochs et al.

[11] Patent Number: 5,908,039
[45] Date of Patent: Jun. 1, 1999

[54] DENTAL FLOSS HAVING IMPROVED FRAY AND SHRED RESISTANCE

[75] Inventors: Harold D. Ochs, Flemington; John Chodzko, East Brunswick; Vipul Davé, Belle Mead, all of N.J.

[73] Assignee: McNeil-PPC, Inc., Skillman, N.J.

[21] Appl. No.: 09/122,122

[22] Filed: Jul. 24, 1998

[51] Int. Cl.$^6$ .................................................. A61C 15/00
[52] U.S. Cl. .......................................... 132/321; 429/49
[58] Field of Search .................................... 132/321, 323, 132/325, 327, 326, 328, 329; 424/49, 50, 52

[56] References Cited

U.S. PATENT DOCUMENTS

| | | | |
|---|---|---|---|
| 5,209,251 | 5/1993 | Curtis et al. | 132/321 |
| 5,226,435 | 7/1993 | Suhonen et al. | 132/321 |
| 5,357,990 | 10/1994 | Suhonen et al. | 132/321 |
| 5,765,576 | 6/1998 | Dolan et al. | 132/321 |
| 5,800,823 | 9/1998 | Blass | 424/49 |

*Primary Examiner*—Gene Mancene
*Assistant Examiner*—Pedro Philogene
*Attorney, Agent, or Firm*—Lawrence D. Schuler; Frederick L. Herman

[57] ABSTRACT

A dental floss comprising a multifilament yarn having at least one coating applied thereon. The yarn comprising the floss is substantially untwisted and comprises entanglement nodes having a frequency of between about 0.5 and about 3.5 inches. The yarn has a basis weight between about 500 and about 1200 denier. The coating applied to the yarn comprises a water-insoluble binder. Optionally, the floss may be coated with a second coating material comprising a water soluble substance such as polyethylene glycol for delivery of additives or additional flavors. With little or no twist and an optimum degree of air-entanglement, the yarn is held together loosely enough to allow a significant amount of coating material to be impregnated between the filaments but tight enough to provide shred and fray resistance and still have supple feel.

34 Claims, 4 Drawing Sheets

DENTAL FLOSS HAVING IMPROVED FRAY AND SHRED RESISTANCE

FIELD OF THE INVENTION

The present invention relates to an improved dental floss. The floss of the invention has improved fray and shred resistance relative to prior art floss, slides easily between teeth and is gentle on the gums.

BACKGROUND OF THE INVENTION

The use of dental floss is recommended by virtually all dental health practitioners According to the Council on Dental Therapeutics, dental flossing has been shown to be 80% effective in removing interdental plaque, yet only about 12% of the United States population use floss regularly. Many consumers find floss to be inconvenient, hard to hold, hard to get between teeth and have problems with the floss fraying and shredding during use. For this reason, floss producers have been seeking ways of making floss easier and more pleasant to use. Unfortunately, most solutions are not particularly efficient and add significant cost to the product.

One approach that has resulted in reduced fraying and shredding is the use of polytetrafluoroethylene (PTFE) monofilament yarn for floss. Unfortunately, PTFE yarns are approximately ten times more expensive than the traditional nylon yarn and its use more than doubles the cost of the floss to the consumer. PTFE floss products are supplied by Gore, Colgate and the Personal Products Company division of McNEIL-PPC, Inc. These products have set the standard for fray and shred resistance. However, PTFE monofilament floss is difficult to provide with adequate flavor because it does not have adequate surface area to carry the flavors. PTFE floss is difficult for the consumer to hold while flossing because it has a low coefficient of friction, and many consumers feel it does not clean between teeth as well as conventional multifilament floss.

A second approach is described in U.S. Pat. No. 5,226,435 and U.S. Pat. No. 5,357,990 assigned to Gillette Canada, Inc. These patents describe a dual-coated, flattened or shaped product using conventional multi-filament yarn. According to these patents, the yarn is initially coated with a first wax and is subsequently coated with a second wax, the melting temperature of the first wax being higher than the melting temperature of the second wax. The first wax coating binds the filaments of the multi-filament yarn together after which it is flattened or shaped. The second coating contains flavor and/or other additives. This product is significantly less expensive than PTFE, but has more flavor impact than some commercially available PTFE monofilament floss. While floss made according to these patents passes more easily between teeth than some other conventional flosses, for many consumers, this product is too thin, does not have the flavor impact of conventional flosses and does not provide the fray/shred resistance of PTFE.

European Patent Application EP 0 790 040 A1 to Ranir/DCP Corp. discloses a dental floss made from high molecular weight polyethylene yarn having a coefficient of friction of less than about 0.2 and a tensile modulus of about 200 to about 2500 grams per denier. The yarn is preferably coated with a coating material such as a wax. The Ranir patent asserts that the properties of the floss disclosed therein are expected to translate into easier insertion between teeth and less fraying and shredding. Our tests show that the force required to pass floss believed to manufactured in accordance with the '040 patent between teeth is equivalent to most conventional multifilament flosses and higher than PTFE monofilament floss. Further, our tests show that this product frays and shreds more than PTFE products. This floss is also significantly more expensive than conventional nylon multi-filament floss since it comprises a yarn whose cost is about 6 times the cost of nylon yarn.

By "shredding," we mean the breaking of yarn filaments of the floss during use. By "fraying," we mean the permanent separation of adjacent filaments of the floss during use. Frayed floss often results in the filaments becoming stuck between teeth, especially between teeth containing restorations.

Manufacturers of prior art flosses have twisted the substrate yarn to prevent fraying. It is well known that fraying of a yarn generally increases as the number of twists per inch decreases (see for example, "Oral Hygiene Products and Practice," by Morton Pader, Marcel Deckker, Inc., New York, 1988, pages 181–182), While adding twist does indeed reduce fraying, increasing the twist of the floss increases its diameter, thereby making it more difficult to pass between teeth.

Bragg (U.S. Pat. No. 4,151,851) discloses that adding twist to floss "causes the strand to be substantially cylindrical in cross section with the strand having a width much larger than individual filaments. Such floss may be difficult to insert between a person's teeth when the teeth fit closely against each other. It has been found that if the twist is removed so that the individual filaments lie parallel to the longitudinal axis of the strand, . . . , the strand will be flat or ribbon shaped, as shown, with a thickness that may be on the order of 0.0005". Such a flat strand, when present edgewise will be easier to insert between closely fitting teeth." While Bragg discloses that a flat tape-like floss will pass more easily between teeth, he does not teach how to prevent shredding or fraying of the yarn.

In light of the continued deficiencies in prior art floss, it is an object of the invention to provide a floss with improved fray and shred resistance.

It is another object of the invention to provide a floss which slides easily between teeth while providing the user with the perception of effectively cleaning between the teeth.

It is another object of the invention to provide a floss which is easy to handle and is gentle on the fingers and gums.

It is another object of the invention to provide a floss that can carry large amounts of flavors and/or other additives.

It is a further object of the invention to provide a floss with all of the above-mentioned attributes.

SUMMARY OF THE INVENTION

The present invention is a dental floss comprising a multifilament yarn having at least one coating applied thereon. The yarn comprising the floss of the invention is substantially untwisted and comprises entanglement nodes having a frequency of between about 0.5 and about 3.5 inches. The yarn has a basis weight between about 500 to about 1200 denier. The coating applied to the yarn comprises a water-insoluble binder. The floss may also be coated with a second coating material which, if used, preferably comprises a water-soluble substance, typically a polymer such as polyethylene glycol, for delivery of additives or additional flavors. With little or no twist and optimum air-entanglement, the yarn is held together loosely enough to allow a significant amount of coating material to be impregnated between the filaments but tight enough to provide shred and fray resistance and still have supple feel.

DETAILED DESCRIPTION OF THE INVENTION

Figure 1:
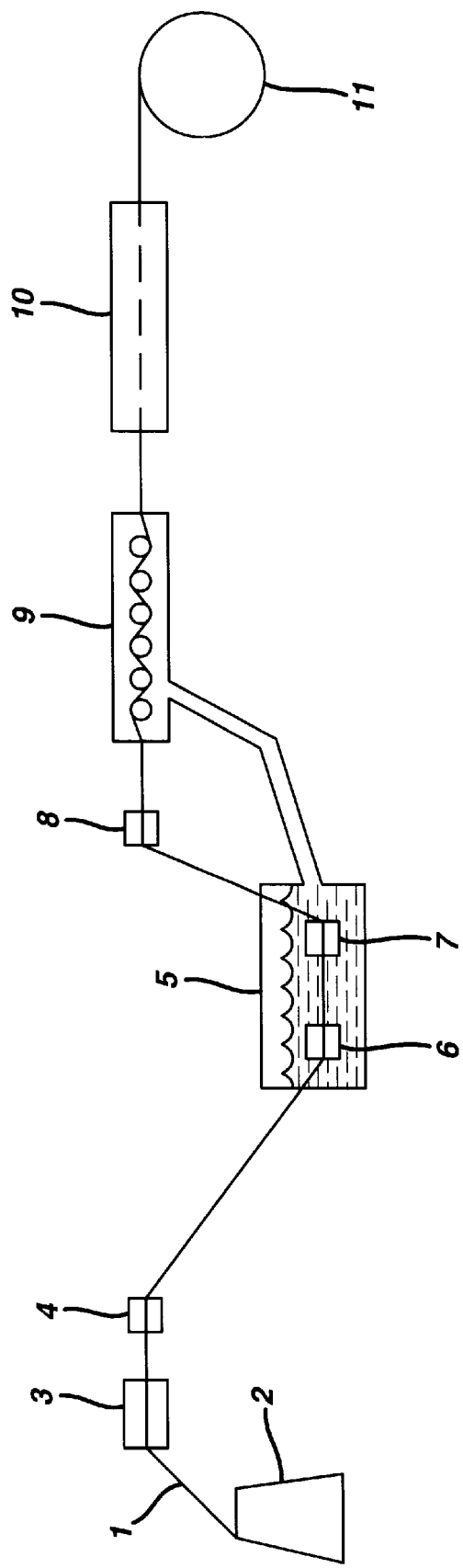
FIG. 1 shows a schematic drawing of an apparatus used to make the floss of the invention.

The floss of the invention is constructed of a multi-filament yarn made with fine filaments with as little twist as possible and with a controlled amount of air-entanglement or air-tacking of the fibers. This yarn is coated with a binding agent, or binder, which comprises a water-insoluble wax such as microcrystalline wax to which flavors and additives may be added. The floss may also be coated with a second coating comprising water soluble wax such as polyethylene glycol for delivery of additives or additional flavors. With little or no twist and optimum air-entanglement, the yarn is held together loosely enough to allow a significant amount of coating material to be impregnated between the filaments but tightly enough to provide shred and fray resistance and still have supple feel.

The floss of the invention is supple, by which we mean that it is soft, flexible and pliant. A supple floss is one which is gentle on the gums and hands, easy to hold, and slides easily between teeth because it complies to fit between tight surfaces between the teeth. The factors that affect suppleness include filament basis weight (related to filament diameter), degree of twist, degree of entanglement and the elastic modulus of the material from which the yarn is made. As used herein, the term "basis weight" as used to describe filaments, yarns and flosses refers to the weight of the article (in grams) of 9000 meters of the article. The weight in grams of 9000 meters is sometimes referred to as "denier". As the filament diameter decreases for a multifilament yarn of a given basis weight, the floss will be able to pass through tight spaces more easily because the individual filaments slide past each other. For example, a first floss may be comprised of a 630 denier yarn, each filament having a basis weight of 6 denier. This yarn comprises 105 filaments. A second floss may be comprised of a second yarn also having a basis weight of 630 denier, each filament having a basis weight of 3 denier. This second yarn comprises 210 filaments. While both yarns have the same overall basis weight, floss made from the second yarn will pass more easily between the teeth because the smaller diameter filaments slide more easily past each other. Also, the smaller the filament diameter, the lower will be the bending modulus per filament and the bending modulus for the yarn as a whole, thereby making the floss softer and more flexible. As the degree of twist and/or entanglement of the yarn increases, the resulting floss becomes less supple because the filaments are unable to slide as the floss is inserted into tight interproximal spaces.

In general, the floss becomes more supple, i.e., softer and more flexible, as the elastic modulus of the polymer from which the yarn is made decreases. However, as will be apparent to those skilled in the art, the elastic modulus must be sufficient to allow the filaments to function as a floss without breakage during use.

In addition to being supple, the floss of the invention also has a high degree of fray and shred resistance. As indicated above, by "shredding," we mean the breaking of yarn filaments during use. By "fraying," we mean the permanent separation of adjacent filaments of the floss during use. Frayed floss often results in the filaments becoming stuck between teeth, especially in the presence of restorations.

The floss of the invention is made from entangled or tacked yarn. Fray and shred resistance is imparted to the floss of the invention by, among other things, carefully controlling the extent of entangling or tacking of the yarn from which the floss is made. The yarn is entangled by impinging a fluid, preferably air, on a yarn as it passes through an entangling device. The entangled yarn contains nodes of entangled fibers spaced along its length. The extent of entanglement, i.e, the frequency and the size of the entanglement nodes, may be adjusted using entangling devices of different design and by varying the pressure of the fluid flowing through the entangling device. As the amount of entanglement of a floss yarn increases, the floss becomes more fray and shred resistant. The higher the amount of entanglement, the closer and more pronounced are the entanglement nodes. As the nodes become more closely spaced, the yarn becomes more round in cross-section, less supple, and, at very high levels of entanglement, the nodes will be felt as bumps. For use as a floss, yarns with excessive entanglement are not desirable. In the floss of the invention, the amount of air-entanglement is optimized. The nodes are close enough to prevent the floss from shredding and fraying during use but not too close to make the floss feel thick and difficult to pass between teeth. When optimized, the use of air-entanglement allows the yarn and floss derived therefrom to conform to the spaces between teeth, which allows the floss to pass easily between the teeth, while at the same time providing the required degree of shred resistance. In the floss of the invention, the entanglement frequency, expressed as the average distance between nodes, is preferably between about 0.5 to about 3.5 inches. More preferably, the entanglement frequency is between about 0.7 to about 2.5 inches, and most preferably, between about 0.9 and about 1.3 inches.

Choosing the optimum filament diameter for the air-entangled floss is also extremely important. The filament diameter is directly related to the basis weight of the filament (expressed in denier, which is the weight in grams of 9000 meters of filament). The smaller the filament diameter, the smaller will be the filament basis weight. As the filament diameter decreases, the floss will feel more supple and gentle to the gums. However, as the filament diameter decreases, the filaments become weaker and are more apt to break and/or shred during use. On the other hand, smaller diameter filaments are easier to air-entangle, requiring less air pressure and the associated nodes are smaller than those obtained when using higher basis weight (larger diameter) filaments. To achieve the best balance between suppleness and strength, the filaments comprising the floss of the invention should have a basis weight of between about 1 to about 5 denier. More preferably, the filament basis weight should be between about 2 and about 4 denier, and most preferably, between about 2.5 to about 3.5 denier.

The strength of the filaments may be expressed in terms of tenacity, defined as the force to break the filaments, i.e., breaking force (in grams) divided by the filament basis weight (in denier). To prevent the floss filaments from breaking during use, the filaments should have a tenacity of at least about 3 grams/denier, preferably, at least about 5 grams/denier, and more preferably, at least about 7 grams per denier. Materials which satisfy this tenacity requirement and which may be used in the floss of the invention include the polyamides, for example, nylon-6 and nylon-6,6; polyolefins, for example polypropylene and polyethylene; and polyesters such as polyethylene terephthalate.

A measure of the "fineness" of the yarn comprising the floss of the invention is the yarn basis weight. The yarn basis weight (expressed in denier) will affect such properties as the ease of passing between teeth, perception of cleaning between teeth, strength, and gentleness of the floss on the gums. As the overall basis weight of the yarn decreases, the floss will pass more easily between teeth. However, decreasing the basis weight below an acceptable value will decrease the floss strength, reduce the perception of cleaning between teeth and will be harsher on the gums. To balance these properties, the floss of the invention preferably comprises a yarn having a basis weight of between about 500 and about 1200 denier. More preferably, the yarn should have a basis weight between about 550 and 850 denier, and most preferably, between about 550 and about 700 denier.

As indicated above, yarns used in prior art flosses have been twisted to prevent fraying. It is well known that fraying of a yarn generally decreases as the amount of twist of the yarn increases. While providing twist does indeed reduce fraying, increasing the twist of the floss also has the effect of increasing its diameter, thereby making it more difficult to pass the floss between teeth. We have discovered that in contrast to the teachings of the prior art, the floss of the invention can be made to be fray and shred resistant without imparting any twist to the yarn.

The floss of the invention is substantially untwisted. The starting yarn used to make the floss of the invention is substantially untwisted. The yarn is removed from its supply spool and is subjected to various coating and re-winding operations during manufacture of the floss. Some slight degree of twist may be imparted to the yarn as it is removed from the supply spool, typically an average of about one twist per linear foot (i.e., about 0.083 twist per inch). As used herein, the term "substantially untwisted", whether used to characterize the starting yarn or the finished floss made from that yarn, means that the twist does not exceed about 1.3 twists per linear inch (tpi). The beneficial effects of the floss of the present invention are obtained when the twist of the floss is not more than about 1.3 tpi. Twist beyond this value makes it more difficult for the floss to pass between tight teeth. Preferably, the floss of the invention and the yarn used to make the floss have a degree of twist of less than about 0.5 tpi.

The floss should have a thickness between about 3 to about 5 mils, and preferably about 4 mils.

To slide more easily between teeth, the floss of the invention preferably has a non-circular cross-section. The aspect ratio (width to thickness) of the floss will depend on the filament size, the degree of twist and the degree of entanglement. The aspect ratio of the floss of the invention should be at least about 8:1 and more preferably, at least about 11:1. The aspect ratio of the floss can be up to about 50:1.

Dental flosses are most typically made by applying coatings to yarns. The coatings serve to adjust the coefficient of friction of the floss, to bind the filaments together in multifilament constructions, and to act as a carrier for flavors and/or other additives. Due to its small filament diameter and resulting high surface area, low degree of twist and optimal degree of entanglement, the floss of the invention can carry significantly more coating than prior art multifilament and monofilament flosses. Prior art monofilament flosses can only generally accommodate no more than about 25% by weight of a coating material based on the weight of the uncoated monofilament substrate. Similarly, prior art multi-filament floss typically has no more than about 50% by weight of a coating material based on the weight of the uncoated yarn. In contrast, the substantially untwisted yarn used to make flosses of the present invention can accommodate a coating of up to about 100% or more by weight based on the weight of the uncoated yarn.

The floss of the invention carries a coating at an add-on of at least about 15 percent by weight based on the weight of the uncoated yarn. Preferably, the coating add-on is from about 40 to about 80% by weight, and more preferably, between about 65 to about 80 percent by weight based on the weight of the uncoated yarn.

The coating used in the floss of the invention comprises a water-insoluble binder. Exemplary binders include synthetic waxes such as microcrystalline wax, natural waxes such as beeswax, low molecular weight polyethylenes having a number average molecular weight between about 1,000 and 5,000, or combinations of such waxes. An exemplary material useful as a binder in the floss of the invention is Multiwax W-445 made by the Petroleum Specialties Group of Witco Corp. of New York, N.Y.

The binder preferably has a melting temperature of at least about 50° C.

In order to maintain the fray resistance of the floss, the add-on of the binder should be at least about 15 percent by weight, preferably at least about 25% by weight, and most preferably, at least about 60 percent by weight based on the weight of the uncoated yarn.

As indicated above, the coatings on the floss may contain flavors or other additives. Flavors may consist of natural or synthetic flavor oils. The flavors may be used as is or they may be encapsulated or supported on a carrier such as starch or modified starch. The supported flavors may be made by spray drying or by other suitable techniques. Because the floss of the invention can carry significantly more coating material than prior art flosses, the floss of the invention can carry two to five times more flavor than prior art flosses, thereby having a greater flavor impact and a better flavor perception to consumers.

The floss of the invention may be provided with an active component such as, for example, a dentifrice or a pharmacological component. The active component may be incorporated into the floss as an additive in the coating.

The dentifrice is preferably a fluoride or fluoride-containing compound such as sodium fluoride, potassium fluoride, ammonium fluoride, sodium difluoride, potassium difluoride, ammonium difluoride, sodium silicofluoride, zinc fluoride, and stannous fluoride. Other dentifrices include, for example, ureases, acid phosphates, calcium carbonate, and magnesium carbonate. Examples of the acid phosphates which may be used include, for example, orthophosphoric acid, monosodium phosphate, monopotassium phosphate, disodium phosphate, dipotassium phosphate, monoammonium phosphate, hemisodium phosphate and sodium hexametaphosphate salts.

Other active components which may be incorporated within the floss include peroxides such as calcium peroxide or hydrogen peroxide or complexes of other materials containing hydrogen peroxide; tooth acidulating agents such as buffered or acidulated phosphofluoride, sodium monofluorophosphate, plaque control agents, tartar control agents such as tetrasodium pyrophosphate, antibiotics to treat pyorrhea and gingivitis, teeth whitening and bleaching agents, pH buffering agents, antifungal agents, remineralizing agents, hemostatic agents, immunological agents and ionic and nonionic antibacterials such as alkyl trimethyl ammonium bromide, chlorhexidine, sanguinaria, triclosan (nonionic), zinc sulfate, tetracycline, cetyl pyridinium chloride, and benzethonium chloride. Additional active components include vitamins, such as Vitamin A, surfactants and emulsifiers. Among the pharmacologically active agents which may be included are, for example, anti-cancer agents, stimulants, bone growth agents, antigens, hormones, steroids, anti-inflammatory agents and analgesic agents. In a further embodiment, the active agent may be a coagulant to inhibit any bleeding which may be produced by flossing. Although the flosses of the invention are less prone to cause bleeding than conventional prior art flosses, some bleeding may occur when the user has sensitive gingival tissue. Preferably, the coagulant is mixed in the wax coating so as to directly contact the gum tissue. The coagulants may include vitamin K, calcium ions in the form of water-soluble calcium salts and blood factors that initiate the coagulation cascade. It is possible to incorporate other coagulants from solution in finely dispersed form in the wax coating medium.

Dental floss of the invention comprises at least one coating comprising a water insoluble binder. The coating comprising the water insoluble binder may also comprise one or more of the aforesaid flavors and/or other additives. Alternatively, the floss of the invention may comprise more than one coating. If the floss comprises multiple coatings, it is preferred that the first coating comprise the water-insoluble binder. Additional coatings, if such are used, preferably comprise a water-soluble carrier such as polyethylene glycol of molecular weight from about 1000 to about 8000, and preferably from about 1000 to about 3500, or polyvinyl alcohol or combinations thereof. If multiple coatings are used, the aforesaid flavors and other additives may be contained in any of the coatings. For example, the floss of the invention may contain two coatings, a first coating comprising water insoluble binder such as microcrystalline wax and a flavor additive, and a second coating comprising polyethylene glycol and sodium fluoride.

Yarn used in the floss of the current invention is made by typical material spinning processes described in the literature. The yarn may be spun in a single step starting with resin and ending in finished product. The resin is heated and extruded through a multi-hole spinneret die. For every hole in the die, a filament of material is generated. The filaments are air quenched (solidified) as they pass through the air space between the end of the die and the first roller of the drawing operation.

Following quenching, a non-toxic, generally recognized as safe spin finish material is applied to the yarn at a rate of about one to two percent of spin finish based on the weight of the yarn. The spin finish lubricates the filaments during subsequent processing.

Following extrusion, the yarn is drawn between a number of godets or rollers. These are typically heated godets followed by non-heated godets turning at a higher speed. The speed differential draws the yarn and increases its tensile strength. Sets of godets may be in series to allow the material to be drawn in stages. Alternatively, the yarn may be drawn in heated ovens. For the yarns used in the floss of the invention, the yarn is typically drawn to a draw ratio of about 6 to 7 times its original length.

Following the drawing operation, the yarn passes through a fluid-entanglement nozzle, air or other suitable gas being the preferable entangling fluid. In the air-entanglement nozzle, turbulent air impinges on the yarn so as to first separate the filaments and to subsequently cause the filaments to re-combine. As the filaments re-combine, they become entangled, forming entanglement nodes at a periodic frequency along the length of the yarn. The degree of entanglement, as indicated by the frequency of entanglement nodes, is a function of the design of the entanglement nozzle and the pressure and nature of the fluid. An exemplary nozzle is triangular slot jet Model 133 available from International Machine Sales, Inc. of Winston-Salem, N.C.

Following fluid entanglement, the finished yarn is then wound on to spools. Yarn used to make the floss of the invention and having the required degree of entanglement can be provided by the yarn manufacturer(s).

The yarn may also be manufactured in a two step process wherein the yarn is first extruded, air quenched and then rewound. It is then passed on to a draw frame where the yarn passes over alternating heated and non-heated godets where the material is drawn. Just before it is rewound, the material is air-entangled.

The characteristics, properties and methods of making the floss of the invention will now be illustrated by the following examples:

EXAMPLE 1

A floss of the invention was made by applying a coating of Multiwax W-445 (Witco) microcrystalline wax to an uncoated yarn using the apparatus shown in FIG. 1. The yarn, obtained from DuPont Canada of Mississauqa, Ontario as Type 769, had the following characteristics:

Yarn Basis Weight: 630 denier

Filament basis weight: 3 denier

Yarn tenacity: 7 grams (force)/denier

Yarn composition: nylon-6,6

Yarn twist: 0

Average distance between entanglement nodes: 1 inch

Figure 2:
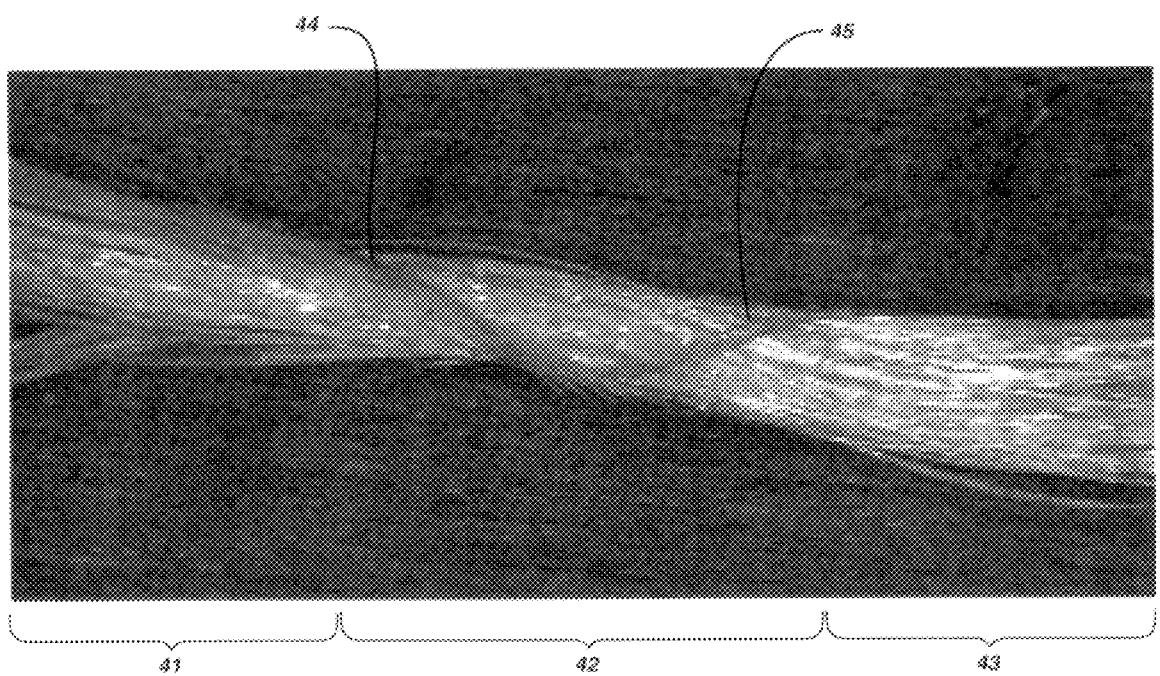
FIG. 2 is a photomicrograph, at a magnification of 20×, showing an entanglement node in the yarn that comprises the floss of the invention.

A photomicrograph of a section of the yarn used in making the floss of Example 1 is shown in FIG. 2. As shown in the figure, the floss section consists of three subsections, 41, 42 and 43. All of the filaments comprising the yarn in subsections 41 and 43 are running substantially parallel to each other along the longitudinal axis of the yarn. Subsection 42 contains an entanglement node in which groups of filaments 44 and 45 are not running parallel to the longitudinal axis of the yarn. Rather, groups of filaments 44 and 45 deviate from the yarn axis and are entangled with each other as well as being "tucked" into the bulk of the yarn. This entanglement decreases the yarn cross-sectional area, makes its shape more round in cross-section, increases its density and anchors the filaments at the entanglement node.

The floss was made as follows:

Referring to FIG. 1 of the accompanying drawings, yarn 1 was unwound from the supply roll 2, tensioned with tensioner 3 and passed through eyelet 4. The yarn was then passed into bath 5 containing the wax (binder) heated to a temperature of (190° F.), and then through eyelets 6, 7, and 8. Excess coating was removed from the floss by passing it over heated rolls 9. The yarn was then passed through chilled tunnel 10 containing air cooled to 37° F. and the resultant floss was rewound onto take-up roll 11 using conventional winding equipment. The floss contained the wax binder at an average add-on of 41 mg per yard, representing a percentage add-on of 65% of binder based on the weight of the uncoated yarn.

Comparative Example 1

Floss was prepared by coating Multiwax W-445 in the manner of Example 1 on yarn having the following characteristics:

Yarn Basis Weight: 840 denier
Filament Basis Weight: 6 denier
Yarn tenacity: 8.6 grams (force)/denier
Yarn composition: nylon-6,6
Yarn twist: 1.7 twists per inch
Average distance between entanglement nodes: 6 inches The floss contained the wax binder at an add-on of 29 mg per yard, representing a percentage add-on of 35% of binder based on the weight of the uncoated yarn.

Comparison of the characteristics and consumer preferences of the flosses of Example 1 and Comparative Example 1 are shown in Tables 1 and 2, respectively.

TABLE 1

Floss Characteristics

| Floss Characteristics | Floss of Example 1 | Floss of Comparative Example 1 |
|---|---|---|
| Yarn Basis Weight: (denier) | 630 | 840 |
| Filament Basis Weight: (denier) | 3 | 6 |
| Yarn tenacity: (grams (force)/denier) | 7 | 8.6 |
| Yarn composition: | Nylon-6, 6 | Nylon-6, 6 |
| Yarn twist: (twists/inch) | 0 | 1.7 |
| Average distance between entanglement nodes: (inches) | 1 | 6 |
| Filament Tensile strength (grams force) | 21 | 52 |
| Binder add-on (mg/yd) | 41 | 29 |
| Binder add-on (wt. % based on weight of uncoated yarn) | 65 | 35 |

Samples of each of the flosses of Examples 1 and Comparative Example 1 were given to 50 test panelists for a two week test. Half the panelists were instructed to use the floss of Example 1 for the first week followed by the floss of Comparative Example 1 for the second week. The other half of the panelists were instructed to use the floss of Comparative Example 1 first followed by the floss of Example 1. Preferences were provided by 46 of the 50 panelists, which are summarized in Table 2.

TABLE 2

Consumer Panel Preferences

| Attribute | Number of Panelists Preferring Floss of Comparative Example 1 | Number of Panelists Preferring Floss of Example 1 | No Preference | Significance (preferring floss of Example 1 over floss of Comparative Example 1) |
|---|---|---|---|---|
| Overall Preference | 8 | 21 | 17 | Significant at $p < .10$ |
| Slides Easily Between Teeth (2 panelist did not answer question) | 8 | 21 | 15 | Significant at $p < .10$ |
| Not Shredding or Fraying | 6 | 19 | 20 | Significant at $p < .10$ |
| Not hurting fingers during use | 3 | 16 | 27 | Significant at $p < .10$ |
| Gentle on Gums | 6 | 14 | 25 | Directional win but not significant at 90% confidence |

Surprisingly, of the panelists having a preference for one or the other of these flosses with respect to fraying and shredding, 3 out of 4 panelists preferred the floss of the invention, i.e., the floss of Example 1 over the floss of the Comparative Example 1, even though the filaments comprising the floss of Example 1 have a tensile strength less than half the strength of the floss of Comparative Example 1.

As indicated previously, the floss of the invention is supple, by which we mean that it is soft, flexible and pliant. A supple floss is one which is gentle on the gums and hands, easy to hold, and slides easily between teeth because it is sufficiently compliant to fit into tight interproximal spaces. The factors that affect suppleness include filament basis weight (related to filament diameter) degree of twist, degree of entanglement and the elastic modulus of the material from which the yarn is made. As the fiber diameter decreases for a yarn of a given basis weight, the floss will be able to pass through tight spaces more easily as the individual filaments slide past each other. Also, the smaller the fiber diameter, the lower will be the bending modulus per filament as well as the bending modulus for the yarn as a whole, thereby making the floss softer and more flexible. The lower filament basis weight of the floss of Example 1 is believed to be responsible for the suppleness attributes perceived by the panelists relative to the floss of Comparative Example 1.

In general, as the degree of twist and/or entanglement of the yarn increases, the resulting floss becomes less supple because the filaments are unable to slide as the floss is inserted into tight interproximal spaces.

While the floss of Example 1 has less twist than the floss of Comparative Example 1, it has a higher degree of entanglement. The panel preferences indicate that the degree of twist and entanglement of the floss of Example 1 provides a better combination of fray resistance and suppleness and leads to an overall preference for the floss of Example 1 relative to the floss of Comparative Example 1.

EXAMPLE 1 and COMPARATIVE EXAMPLE 2

Flavored Floss

Another floss of the invention was made by applying a coating comprising water-insoluble binder, flavor and sweetener to the yarn used in Example 1. The floss was made using the general method and apparatus of Example 1 and FIG. 1 respectively, with the exception that rather than using a bath, the coating was applied to the yarn via a die that was injected with the requisite amount of coating material. The coating materials used to prepare the floss of Example 2 and Comparative Example 2 were of the compositions shown in Table 3.

TABLE 3

Coating Compositions

| Component | Composition (wt. %) | |
| --- | --- | --- |
| | Example 2 | Comparative Example 2 |
| Multiwax W-445 | 84 | 83 |
| Spray dried flavor (25% flavor oil on 75% modified starch) | 15 | |
| Spray dried flavor (16% flavor oil on 84% modified starch) | | 17 |
| Sodium saccharin | 1 | |

The flosses had the characteristics described in Table 4 below:

TABLE 4

Floss Characteristics

| Floss Characteristics | Floss of Example 2 | Floss of Comparative Example 2 |
| --- | --- | --- |
| Yarn Basis Weight: (denier) | 630 | 840 |
| Filament Basis Weight: (denier) | 3 | 6 |
| Yarn tenacity: (grams (force)/denier) | 7 | 5 |
| Yarn composition: | Nylon 6, 6 | Nylon 6 |
| Yarn twist: (twists/inch) | 0 | 1.7 |
| Average distance between entanglement nodes: (inches) | 1 | Unentangled |
| Filament Tensile Strength (grams force) | 21 | 30 |
| Coating add-on (mg/yd) | 52 | 31 |
| Coating add-on (wt. % based on weight of uncoated yarn) | 79 | 37 |
| Binder add-on (mg/yd) | 44 | 26 |
| Binder add-on (wt. % based on weight of uncoated yarn) | 66 | 31 |

The flosses of Example 2 and of Comparative Example 2 were placed with 53 test panelists of whom 49 responded. The comparative evaluation was conducted as described above. The results of the comparison are shown in Table 5.

TABLE 5

Consumer Panel Preferences

| ATTRIBUTE | Preferring Floss of Comparative Example 2 | Preferring Floss of Example 2 | No Preference | Significance (preferring floss of Example 2 over floss of Comparative Example 2) |
| --- | --- | --- | --- | --- |
| Overall Preference | 15 | 29 | 5 | significant at $p \leq .10$ |

TABLE 5-continued

Consumer Panel Preferences

| ATTRIBUTE | Preferring Floss of Comparative Example 2 | Preferring Floss of Example 2 | No Preference | Significance (preferring floss of Example 2 over floss of Comparative Example 2) |
| --- | --- | --- | --- | --- |
| Having the right amount of flavor | 15 | 24 | 10 | Directionally significant at $.20 \geq p \geq .10$ |
| Slides easily between teeth | 10 | 30 | 9 | Significant a $p \leq .01$ |
| Not fraying/ shredding | 12 | 24 | 13 | Significant at $p \leq .10$ |
| Gentle to the gums | 7 | 22 | 20 | Significant at $p \leq .05$ |
| Having the right thickness | 11 | 23 | 15 | Significant at $p \leq .10$ |
| Cleans effectively between all teeth | 8 | 21 | 19 | Significant at $p \leq .10$ |
| Floss is of high quality | 12 | 24 | 13 | Significant at $p \leq .10$ |

In addition to the attributes of suppleness and shred and fray resistance discussed above, the floss of Example 2 demonstrates a greater consumer-perceived preference for correct amount of flavor relative to the floss of Comparative Example 2. This preference for the floss of Example 2 with respect to flavor is due, at least in part, to the greater loading of coating material which the substantially untwisted yarns used to make the floss of the present invention can accommodate relative to twisted yarns used in prior art flosses.

EXAMPLE 3

Another floss of the invention was made by applying a coating of Multiwax W-445 water-insoluble binder to a polypropylene yarn in the manner described in Example 2. The coating was applied to the yarn at a temperature of 185 to 190° F. The floss and yarn used to make the floss had the characteristics as shown in Table 6.

TABLE 6

Floss Characteristics

| Floss Characteristics | Floss of Example 3 |
| --- | --- |
| Yarn Basis Weight: (denier) | 620 |
| Filament Basis Weight: (denier per filament) | 3 |
| Yarn tenacity: (grams (force)/denier) | 5 |
| Yarn composition: | Polypropylene |
| Yarn twist: (twists/inch) | 0 |
| Average distance between entanglement nodes: (inches) | 0.7 |
| Filament Tensile Strength (grams force) | 15 |
| Coating add-on (mg/yd) | 36 |

TABLE 6-continued

Floss Characteristics

| Floss Characteristics | Floss of Example 3 |
|---|---|
| Coating add-on (wt. % based on weight of uncoated yarn) | 58 |
| Binder add-on (mg/yd) | 36 |
| Binder add-on (wt. % based on weight of uncoated yarn) | 58 |

Panelists were asked to evaluate the floss of Example 3 in comparison to the floss of Example 1 in the manner described above. The results of the comparison are shown in Table 7.

TABLE 7

Consumer Panel Preferences

| ATTRIBUTE | PREFER FLOSS OF EXAMPLE 1 | PREFER FLOSS OF EXAMPLE 3 | NO PREFER-ENCE | Significance (preferring floss of Example 1 over floss of Example 3) |
|---|---|---|---|---|
| Overall Preference | 19 | 19 | 11 | Not Significant |
| Slides Easily between Teeth | 23 | 9 | 16 | Significant at .01 < p < .05 |
| Not shred or Fray | 14 | 9 | 25 | Not Significant |
| Being Gentle to the gums | 16 | 9 | 23 | Not significant |
| Having the right thickness | 12 | 17 | 19 | Not significant |

Panelists exhibited no statistically significant preference for either of the flosses, with the exception of the attribute of sliding easily between teeth, where the floss of Example 1 was preferred. The floss of Example 3 has a somewhat higher degree of entanglement (0.7 inch between nodes) than the floss of Example 1 (1.0 inch between nodes). The higher degree of entanglement causes the floss of Example 3 to be about 0.0005 inch thicker than the floss of Example 1, and this difference in thickness is believed to be responsible for the difference in the perceived ease of sliding between the teeth.

Simulated Floss Use Tests

Figure 3:
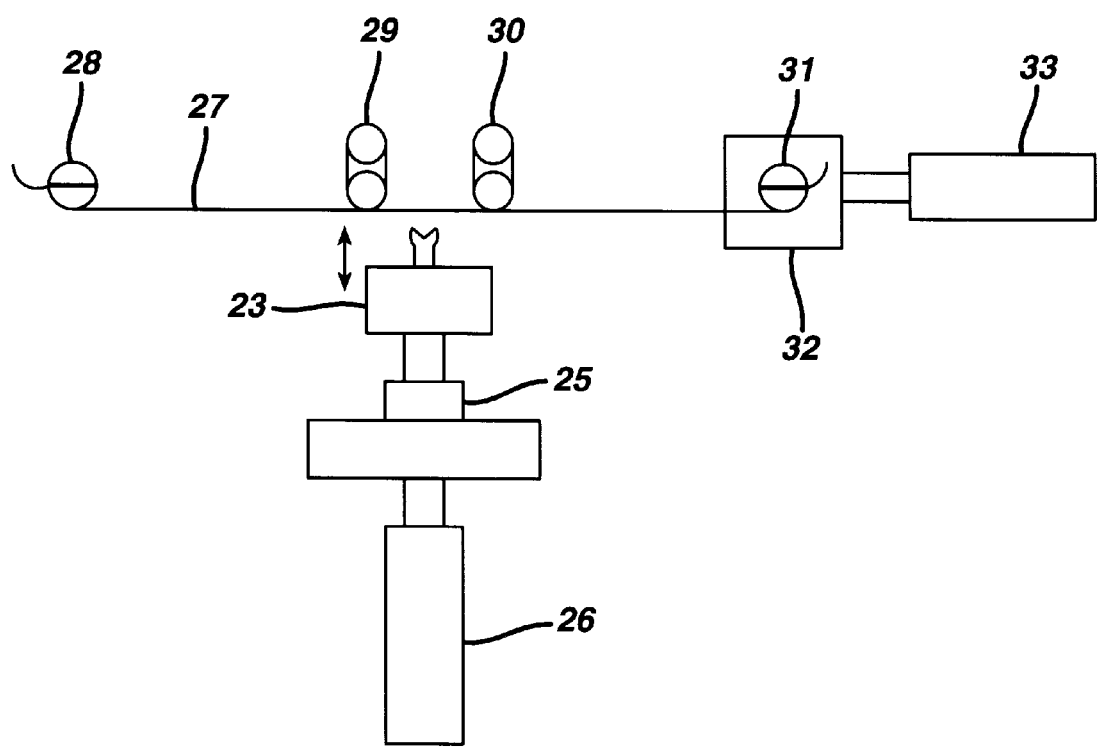
FIG. 3 shows a front view of a test apparatus to evaluate the shred and fray resistance of floss during use.
Figure 4:
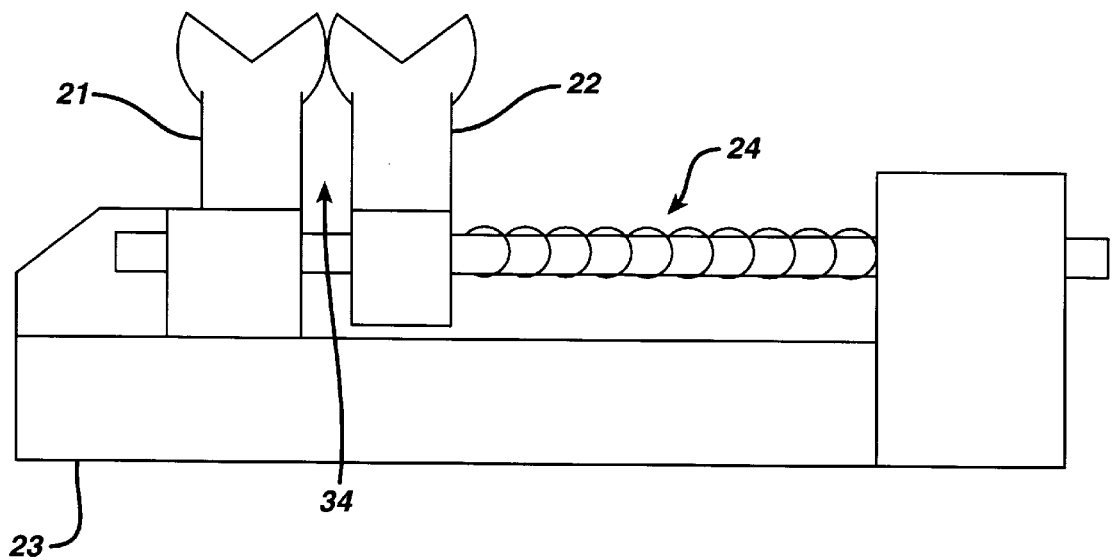
FIG. 4 shows a side view of a tooth-holding fixture used in the apparatus of FIG. 3.

A simulated use test was developed to define the effects of product and process variables on floss properties and to quantitatively differentiate the properties of floss made according to the invention vs. other flosses. The simulated use test provides an indication of the force required to insert a floss between tightly spaced teeth (related to ease of sliding between teeth) and of the fray and shred resistance of the floss. An apparatus to perform these measurements is shown schematically in FIGS. 3 and 4. The apparatus consists of a pair of artificial Ivorine™ teeth 21 and 22 (tooth numbers 2 and 3, second and third upper right molars) available from Columbia Dentoform Corp. of Long Island City, N.Y. The Ivorine teeth are represented by the manufacturer as being anatomically correct and having cutting characteristics similar to natural teeth. The teeth are mounted on assembly 23 and the compressive force between the teeth is adjusted to a value of between 1 and 2 pounds by spring 24. The assembly 23 is mounted on load cell 25 which in turn, is mounted on a double-acting air cylinder 26. A floss sample 27 is wrapped around fixed anchoring pin 28, guides 29 and 30 and anchoring pin 31. Pin 31 is anchored on block 32 which is attached to air cylinder 33 which applies a tension force on the floss of about 1 pound. A "cycle" of floss use is simulated by applying air pressure to air cylinder 26, causing assembly 23 to rise so as to cause the teeth to initially contact the floss and to subsequently cause the floss to pass into the interproximal space 34 between the teeth. The force required to insert the floss between the teeth is measured by load cell 25. Pressure is reversed on the air cylinder 26 causing the assembly 23 to be lowered, thereby removing the floss from the interproximal space. Each sample is subjected to 20 such cycles. The floss insertion force is taken as the average of the insertion forces measured over the first five cycles.

Shredding is indicated by the percentage change in tensile strength between the unused floss and a test sample subjected to 20 insertion cycles as defined above. The percentage change in tensile strength between unused floss and floss subjected to the simulated use test is attributed to filament wearing and breaking during the use test. Thus, the percentage change in tensile strength between the used and unused floss is an indicator of the extent of shredding expected during actual use.

The extent of shredding as determined by the simulated use test for the flosses of the invention versus other commercially available flosses is shown in Table 8 below:

TABLE 8

Tensile Strength of Floss Before and After Simulated Use Test*

| Floss | Tensile Strength of Unused Floss (Pounds) | Tensile Strength After Simulated Use (Pounds) | Change in Tensile strength (Pounds) | Change in Tensile strength (%) |
|---|---|---|---|---|
| Floss of Example 1 | 9.4 | 8.6 | 0.8 | 8.5 |
| Floss of Example 2 | 10.0 | 9.8 | 0.2 | 2.0 |
| Floss of Example 3 | 7.6 | 6.9 | 0.7 | 10.5 |
| Floss of Comparative Example 1 | 15.7 | 11.8 | 3.9 | 24.8 |
| Floss of Comparative Example 2 | 9.5 | 7.3 | 2.2 | 23.2 |
| Oral-B Mint | 6.5 | 3.3 | 3.2 | 49.2 |
| CVS Waxed | 14.4 | 12.8 | 1.6 | 11.1 |
| RiteAid Hi-Tech Mint | 21.0 | 11.9 | 9.1 | 43.3 |
| RiteAid Waxed | 11.7 | 10.2 | 1.5 | 12.8 |
| Glide (monofilament) | 8.4 | 8.2 | 0.2 | 2.3 |

*(Teeth loaded at 1.25 lbs)

As indicated by the data in Table 8, the flosses of the invention have superior shred resistance as indicated by the simulated use tests relative to the comparative examples. They are also superior or comparable to other commercially available multi-filament flosses.

The simulated use test also provided data on the force required to insert the floss between the teeth. These data are shown in Table 9 below:

TABLE 9

Floss Insertion Force Data*

| FLOSS | Mean Insertion Force (grams) and (Standard Deviation) |
| --- | --- |
| Floss of Example 1 | 602 (32) |
| Floss of Example 2 | 603 (32) |
| Floss of Example 3 | 676 (31) |
| Floss of Comparative Example 1 | 642 (19) |
| Floss of Comparative Example 2 | 682 (13) |
| Oral-B Mint | 437 (22) |
| CVS Waxed | 680 (13) |
| RiteAid Hi-Tech Mint | 765 (52) |
| RiteAid Waxed | 664 (11) |
| Glide (monofilament) | 493 (56) |

*Teeth loaded with two pound compressive force.

The flosses of the invention have a higher insertion force than Glide floss which is composed of PTFE monofilament. They also have higher insertion force than the Oral B product. However, as shown in Table 8, the flosses of the invention are superior to the Oral B product in terms of shred resistance. Thus, the more preferred embodiments of the invention (Examples 1 and 2) offer the best compromise over the prior art products in terms of sliding easily between teeth and shred resistance.

The flosses of the invention were also characterized versus selected flosses of the prior art with respect to twist and degree of entanglement. These data are shown in Table 10.

TABLE 10

Twist and Entanglement-Floss of the Invention vs. Prior Art

| Floss | Twist (twists/inch) | Entanglement (inches between nodes) |
| --- | --- | --- |
| Floss of Example 1 | 0 | 1 |
| Floss of Example 2 | 0 | 1 |
| Floss of Example 3 | 0 | 0.7 |
| Floss of Comparative Example 1 | 1.7 | 6 |
| Floss of Comparative Example 2 | 1.7 | 0 |
| CVS Waxed | 3 | 2.6 |
| RiteAid Waxed | 1.7 | 3.8 |

As indicated earlier, the prior art solutions to floss fraying problems involved twisting the yarn from which the floss was made. The CVS waxed and RiteAid waxed products achieved fray resistance by introducing twist to the yarn. The data in Tables 8 and 10 indicate that the floss of the invention has comparable shred resistance to the best prior art multi-filament floss without resorting to the prior art solution, i.e., twisting the yarn. Rather, the data demonstrate that comparable shred resistance may be achieved using substantially untwisted yarn by controlling the degree of yarn entanglement to values as specified hereinabove.

EXAMPLES 4 and 5

Multiple Coatings

Floss of these examples was made using the yarn described in Example 2 and the coating method of Example 2. In a first coating step, the yarn was unwound from a supply spool, coated with Multiwax W-445 and re-wound. Two flosses were prepared differing in the amount of Multiwax binder applied to the yarn. The amount of binder add-on was controlled by regulating the supply of binder to the coating die. In a second coating step, each of the yarns containing the first coating was again coated using the same equipment and process with a coating material having the following composition:

| Component | Percent by Weight |
| --- | --- |
| polyethylene glycol 1450 | 42 |
| polyethylene glycol 1000 | 42 |
| spray dried flavor | 15 |
| sodium saccharin | 1 |

The characteristics of the resultant floss are shown in Table 11 below.

TABLE 11

Floss Characteristics

| Floss Characteristics | Floss of Example 4 | Floss of Example 5 |
| --- | --- | --- |
| Yarn Basis Weight: (denier) | 630 | 630 |
| Filament Basis Weight: (denier) | 3 | 3 |
| Yarn tenacity: (grams (force)/denier) | 7 | 7 |
| Yarn composition: | Nylon-6, 6 | Nylon-6, 6 |
| Yarn twist: (twists/inch) | 0 | 0 |
| Average distance between entanglement nodes: (inches) | 1 | 1 |
| Filament Tensile strength (grams force) | 21 | 21 |
| Add-on of first coating (binder) (mg/yd) | 7 | 14 |
| Add-on of first coating (binder) (wt. % based on weight of uncoated yarn) | 11 | 22 |
| Add-on of second coating (mg/yd) | 19 | 19 |
| Add-on of second coating (wt. % based on weight of uncoated yarn) | 30 | 30 |

The flosses of Examples 4 and 5 were subjected to the simulated use test described above and samples were photographed after 20 cycles. Microphotographs of the floss of Example 4 after the simulated use test revealed loose fibers on the surface of the floss that might be expected to break in use. In contrast, the microphotographs of the floss of Example 5 containing twice the amount of binder of Example 4 indicated that the surface filaments were more tightly adhered to the bulk of the floss than the floss of Example 4 and would be expected to be more shred-resistant and less likely to be stuck between teeth during use.

We claim:

1. A dental floss comprising a yarn and at least a first coating applied to said yarn, said yarn comprising a multiplicity of filaments and being substantially untwisted, said yarn comprising entanglement nodes, wherein:

said yarn has an entanglement frequency, expressed as the average distance between nodes, of between about 0.5 and about 3.5 inches;

said yarn has a basis weight between about 500 to about 1200 denier; and wherein said first coating comprises a water-insoluble binder.

2. The floss of claim 1 wherein said entanglement frequency is between about 0.7 and 2.5 inches.

3. The floss of claim 2 wherein said entanglement frequency is between about 0.9 to about 1.3 inches.

4. The floss of claim 1 wherein said filaments have a basis weight between about 1 and about 5 denier.

5. The floss of claim 4 wherein the filaments have a basis weight of between about 2 to about 4 denier.

6. The floss of claim 5 wherein the filaments have a basis weight of between about 2.5 to about 3.5 denier.

7. The floss of claim 1 wherein said filaments have a tenacity of at least about 3 grams per denier.

8. The floss of claim 7 wherein said filaments have a tenacity of at least about 5 grams per denier.

9. The floss of claim 8 wherein said filaments have a tenacity of at least about 7 grams per denier.

10. The floss of claim 1 wherein said yarn comprises a polymer selected from the group consisting of polyamides, polyolefins and polyesters.

11. The floss of claim 10 wherein said polyamide is selected from nylon-6 and nylon-6,6.

12. The floss of claim 1 wherein the yarn has a basis weight of between about 550 and about 850 denier.

13. The floss of claim 12 wherein the yarn has a basis weight of between about 550 to about 700 denier.

14. The floss of claim 1 wherein the yarn has a degree of twist of less than about 1.3 twists per linear inch.

15. The floss of claim 14 wherein the yarn has a degree of twist of less than about 0.5 twists per linear inch.

16. The floss of claim 1 wherein the floss has a thickness between about 3 to about 5 mils.

17. The floss of claim 16 wherein the floss has a thickness of about 4 mils.

18. The floss of the claim 1 wherein the floss has an aspect ratio greater than about 8:1.

19. The floss of claim 1 wherein said binder comprises a wax selected from natural waxes, synthetic waxes and mixtures thereof.

20. The floss of claim 19 wherein said wax is selected from microcrystalline wax, beeswax, low molecular weight polyethylenes having a number average molecular weight between about 1,000 and 5,000, and mixtures thereof.

21. The floss of claim 1 wherein said binder has a melting temperature of at least about 50° C.

22. The floss of claim 1 wherein said binder is present in the floss at a level of at least about 15 percent by weight based on the weight of said yarn.

23. The floss of claim 22, wherein said binder is present in the floss at a level of at least about 25 percent by weight based on the weight of said yarn.

24. The floss of claim 23 wherein said binder is present in the floss at a level of at least about 60 percent by weight based on the weight of said yarn.

25. The floss of claim 1 wherein said floss optionally comprises a second coating.

26. The floss of claim 25 wherein said second coating comprises a water soluble carrier.

27. The floss of claim 26 wherein said water soluble carrier comprises a polymer selected from polyethyleneglycol, polyvinylalcohol or mixtures thereof.

28. The floss of claim 25 wherein said floss further comprises at least one additive selected from flavors, dentifrices, peroxides, plaque control agents, tartar control agents, antibiotics, teeth whitening and bleaching agents, pH buffering agents, antifungal agents, remineralizing agents, hemostatic agents, antibacterials, vitamins, surfactants and emulsifiers and analgesic agents.

29. The floss of claim 28 wherein said at least one additive is present in the first coating, in the second coating or in both of said coatings.

30. The floss of claim 25 wherein said coatings are present in the floss at an add-on of between about 15 percent and about 100 percent by weight based on the weight of said yarn.

31. The floss of claim 25 wherein said coatings are present in the floss at an add-on of between about 40 percent and about 80 percent by weight based on the weight of said yarn.

32. The floss of claim 25 wherein said coatings are present in the floss at an add-on of between about 65 percent and about 80 percent by weight based on the weight of said yarn.

33. A dental floss comprising a yarn and at least a first coating applied to said yarn, said yarn comprising a multiplicity of filaments and being substantially untwisted, said yarn comprising entanglement nodes, wherein:

a) said yarn has an entanglement frequency, expressed as the average distance between nodes of between about 0.5 and about 3.5 inches;

b) said yarn has a basis weight between about 500 to about 1200 denier and a tenacity of at least about 3 grams per denier;

c) said first coating comprises a water-insoluble binder, said binder being present in said floss at a level of at least about 15 percent by weight based on the weight of said yarn; and d) each of said filaments having a basis weight between about 1 to about 5 denier.

34. A dental floss comprising a yarn and at least a first coating applied to said yarn, said yarn comprising a multiplicity of filaments, said yarn comprising entanglement nodes, wherein:

a) said yarn has an entanglement frequency, expressed as the average distance between nodes of between about 0.5 and about 2.5 inches;

b) said yarn has a basis weight between about 500 to about 1200 denier;

c) said first coating comprises a water-insoluble binder.

* * * * *